United States Patent
Driskell et al.

[19]

[11] Patent Number: 5,827,062
[45] Date of Patent: Oct. 27, 1998

[54] DENTAL IMPLANT ABUTMENT APPARATUS

[75] Inventors: Thomas D. Driskell, Westerville, Ohio; Vincent J. Morgan, Boston, Mass.

[73] Assignee: Diro, Inc., Boston, Mass.

[21] Appl. No.: 744,330

[22] Filed: Nov. 6, 1996

[51] Int. Cl.$^6$ ............................................. A61C 8/00
[52] U.S. Cl. ............................................. 433/173; 433/172
[58] Field of Search ................................. 433/172, 173, 433/174, 175

[56] References Cited

U.S. PATENT DOCUMENTS

| | | | |
|---|---|---|---|
| 5,030,095 | 7/1991 | Niznick | 433/174 |
| 5,087,200 | 2/1992 | Brajnovic et al. | 433/174 |
| 5,344,457 | 9/1994 | Pilliar et al. | 433/175 |
| 5,362,235 | 11/1994 | Daftary | 433/173 |
| 5,376,004 | 12/1994 | Mena | 433/173 |

*Primary Examiner*—John J. Wilson
*Attorney, Agent, or Firm*—John A. Haug

[57] ABSTRACT

A two part abutment system (50,50' and 64,64',64") is shown for use with a root member (10) implanted in the alveolar bone (16) particularly suited for use when the root member (10) is not positioned sufficiently deep within the the bone to thereby expose portions of the root member. The abutment member (50,50') is formed with a root member shoulder receiving seat in communication with a bore having at least a portion with a non-circular surface. A post (64,64', 64") having a non-circular head (66) having a shape conforming to that of non-circular portion of the bore and a shank (68) extending therefrom is received through the bore into the socket (28) of the root member (10). Suitable locking means such as cement is used to fix the abutment to the root member. An adaptor (70, 70') is shown for converting a root member (74) having a threaded bore (72) for use with the two part abutment system of the invention. A modified post (84) is show having first and second locking tapers for reception in bores having matching locking tapers formed in the root member and abutment member, respectively.

15 Claims, 3 Drawing Sheets

DENTAL IMPLANT ABUTMENT APPARATUS

FIELD OF THE INVENTION

This invention relates generally to restorative dentistry and more particularly to dental implants for surgical implantation in the mouth of a patient and to abutment systems used with such implants.

BACKGROUND OF THE INVENTION

The natural teeth of an individual may be lost as a result of dental disease or trauma, making it desirable to replace such teeth with a prosthetic device. One type of prosthetic device is the dental implant which is surgically positioned within the mandibular or maxillary alveolar bone.

One type of dental implant has a separate root member which is implanted by a dentist in the alveolar bone of a patient. Following healing, a head member, commonly called an abutment, is mounted in or on the root member and a tooth simulating prosthesis or crown is then mounted on the abutment. A successful system of this type is disclosed in U.S. Pat. No. 4,738,623. In that patent, a root member having a first or top end formed with a female socket circumscribed by a shoulder and having suitable anchoring means, such as outwardly extending fins, is placed in a root receiving cavity formed in the alveolar bone with suitable surgical instruments and techniques. The root member is inserted into the cavity with the top portion of the root member a selected distance below the opening of the cavity, that is, below the crest of the bone, e.g., two or three millimeters. A healing plug is inserted into a female socket of the root member and particles of a natural and/or synthetic bone growth stimulating grafting material are then packed within the cavity around the shoulder of the root member and the wound is then closed.

Following healing, the dentist surgically opens access to and removes the plug and replaces it with an abutment. The abutment has a male portion received within the female socket and an intermediate, outer generally hemispherical surface portion which extends through the surface of the gingiva and preferably through the surface of the crest of the bone which previously had been reamed to form a complimentary configuration when forming the cavity. A prosthetic device can then be placed on the abutment forming a smooth continuous surface with the hemispherical surface portion of the abutment with the interface between the prosthetic device and the abutment covered by the gingival tissue.

If for some reason the bone graft does not extend to the outer surface of the bone crest or if the dentist does not form the cavity sufficiently deep so that the vertical position of the root member is too high, the interface between the crown and the abutment, or even the abutment and the root member itself, could be exposed causing an unaesthetical appearance.

SUMMARY OF THE INVENTION

It is an object of the present invention to overcome the above noted limitation of the prior art. Another object of the invention is to provide an abutment for use with a root member which has not been implanted in an optimal relationship in the aveolar ridge of a patient relative to the crest of the bone in order to give a cosmetically pleasing appearance. Yet another object is the provision of an abutment system which can be used with various types of root members.

Briefly, in accordance with the invention, a two part abutment system comprises as a first part an abutment member having a first or basal end formed with a root member shoulder seating surface which communicates with a non-circular post head seat formed in a bore preferably extending through the abutment. The outer surface configuration of the basal end is formed with a generally hemispherical surface portion and a prosthetic component, e.g., crown mounting portion, extends therefrom to a second end. Typically the mounting portion has a generally tapered portion having a generally frusto-conical surface with one or more anti-rotational flats onto which a prosthetic component, such as a crown, is mounted. The second part of the two part abutment system comprises an anti-rotation post member having a non-circular head portion matching that of the post head seat at one end of the member and a locking taper on the post portion extending from the head of the member which is lockably received within a matching tapered female seat in the socket of the root member with the non-circular head of the post received in the post head seat of the abutment member. The abutment member can then be locked to the root member by use of suitable means such as cement placed into the bore over the post head and/or a pin or screw laterally extending through a bore in the head and across the bore in the abutment. According to a feature of the invention, the taper of the root member shoulder seating surface is formed with a different taper from that of the implant shoulder on which the abutment member is received in order to form a cement seal. The bore in the abutment member, which communicates with the post head seat, is coaxial with the longitudinal axis of the root member while the longitudinal axis of the crown mounting portion can be coaxial with the longitudinal axis of the root member or may be at a selected angle therewith, e.g., 15, 25, 30 degrees. Generally, it is preferred to provide a series of abutments with crown mounting portions having several different angles suitable for any given site in order to allow the dentist to align the prosthesis with contiguous natural teeth and/or other implants.

According to a modified embodiment, root members having an internally threaded bore can be converted to use the two part abutment system by use of an adaptor which is a generally tubular member having a threaded or unthreaded outer surface for reception in the root member and a bore with a locking taper for reception of the anti-rotation post member. According to another embodiment the anti-rotation post member is formed with first and second locking tapers extending from a transition location to respective opposite distal ends of the post member so that an abutment member provided with a bore having a locking taper can be locked to a root member using only the double locking tapered post member.

Additional objects and features of the invention will be set forth in part in the description which follows and in part will be obvious from the description. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings.

DETAILED DESCRIPTION OF PREFERRED EMBODIMENTS

Figure 1:
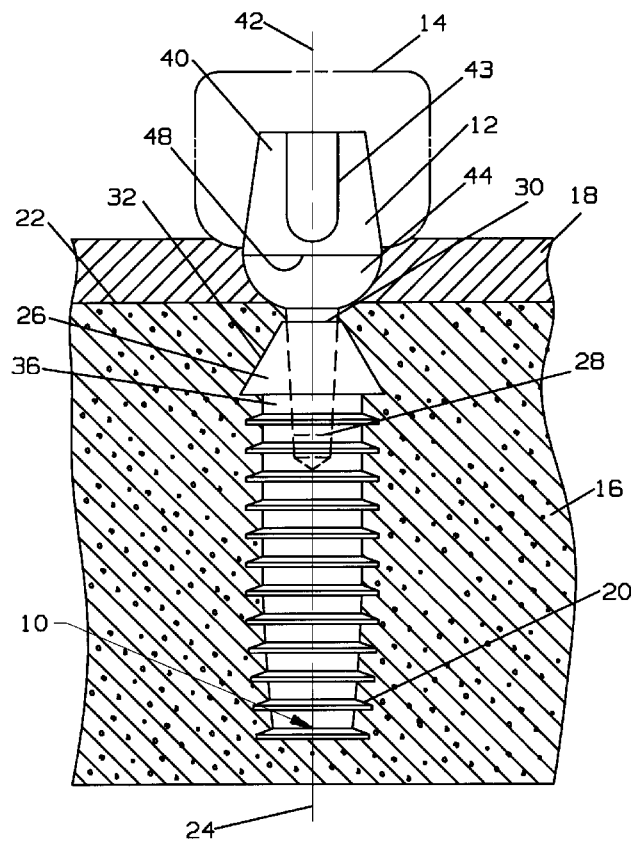
FIG. 1 is a view in vertical section of a dental implant as disclosed in U.S. Pat. No. 4,738,623.

With regard to FIG. 1, a root member 10 is shown upon which an abutment member 12 is mounted. A prosthetic device in the form of a crown 14, shown in dashed lines, is in turn mounted on abutment 12. The root member is implanted in the alveolar bone 16 which is shown covered by gingiva 18.

Root member 10 has a plurality of outwardly extending fins 20 formed on a lower portion of the root member. In the description of the invention, the terms upper and lower are used with respect to depth within the bone and not with respect to the center of the earth. Thus, "lower" refers to a portion of the implant which is implanted deeper within the cavity and "upper" refers to a portion more proximal to the crest 22 of the bone or to the gingiva 18.

A narrowed, upwardly and inwardly extending tapered shoulder 26 extends smoothly and continuously above the fins with the shoulder positioned below the crest 22 of the bone 16 when the root member is properly implanted.

An upwardly opening, post receiving female socket 28 having a longitudinal axis 24, also the longitudinal axis of root member 10, is formed into the root member through the top 30 of shoulder 26. The socket has a generally circular configuration but is formed with a locking taper. Abutment member 12 is provided with a matching tapered post 36. The abutment member 12 is shown having an upstanding, generally frusto-conical portion 40 with one or more anti-rotation flats 43 onto which a prosthetic crown 14 is mounted. The frusto-conical surface 40 has a longitudinal axis 42 which is coaxial with axis 24 in the FIG. 1 structure.

The abutment member 12 has a basal end portion 44 having a convex, generally hemispherical exterior surface portion which extends downwardly from the frusto-conical surface 40. The center of the sphere which defines the generally hemispherical surface portion lies on the axis 42 of the conical surface resulting in the intersection of the hemispherical surface portion 44 and the frusto-conical surface 40 along a circle 48.

The dentist surgically implants the root member by forming a root receiving cavity within the alveolar bone 16. This cavity is drilled and reamed using appropriate surgical instruments and techniques. The root member 10 is inserted within the cavity with the top 30 of the shoulder 26 a selected distance of several millimeters below crest 22 of bone 16. A healing plug is inserted into the female socket 28 and trimmed to the proper height. Particles of material of natural and/or synthetic bone growth stimulating grafting matrial are then packed within the bore below the crest and around the shoulder 26. The wound is then closed by suturing and allowed to heal.

Following healing, the dentist surgically opens access to and removes the plug and replaces it with the abutment member 12 as illustrated in the Figure. When the root member 10 is properly positioned vertically with respect to the crest 22 of aveolar bone 16, the abutment member is positioned so that the hemispherical surface portion 44 extends below the surface of the gingiva 18 and preferably in through the crest 22 of the bone 16 which has been reamed to a complimentary configuration.

Figure 2:
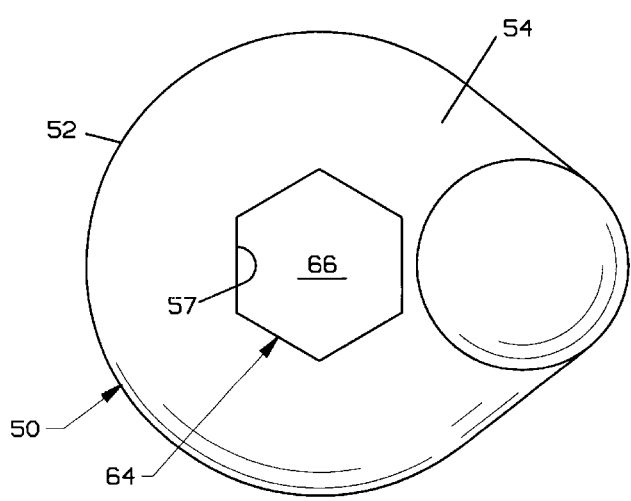
FIG. 2 is a top plan view of a two part abutment for mounting on the abutment made in accordance with a first embodiment of the invention.
Figure 3:
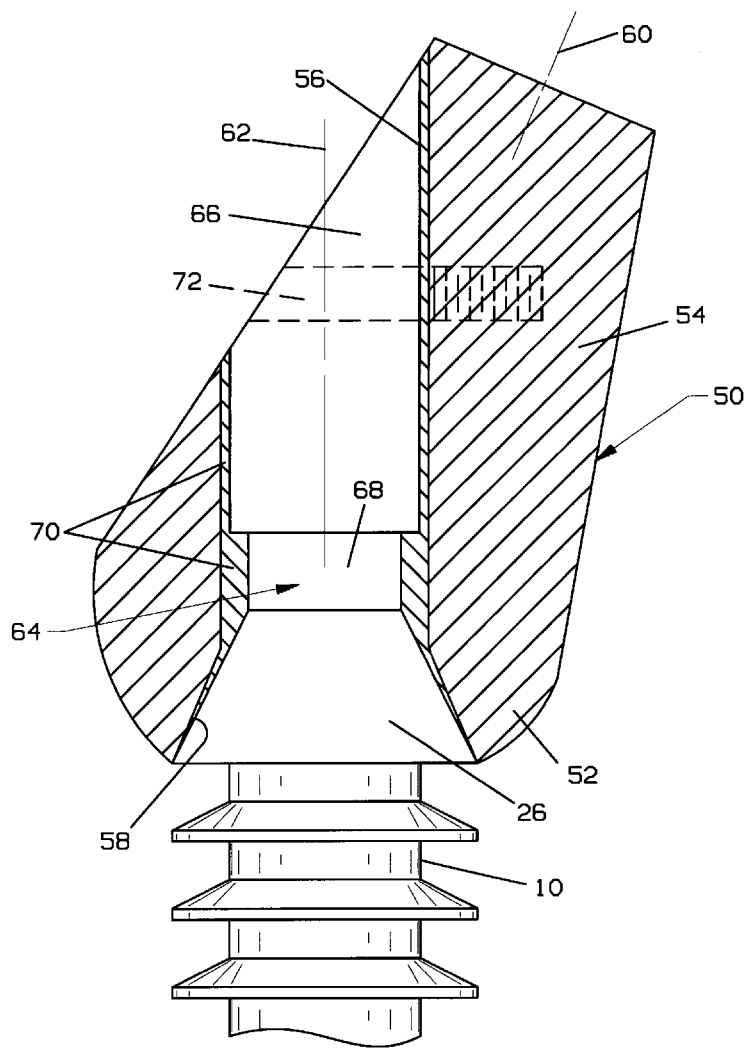
FIG. 3 is a view in vertical section of the FIG. 2 two part abutment shown mounted on a root member (partially shown)
Figure 4:
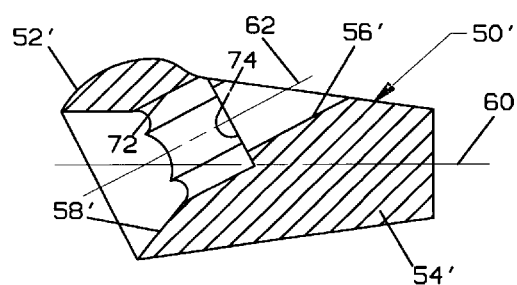
FIG. 4 is a sectional view taken through an abutment member made in accordance with a modified embodiment of the invention.
Figure 5:
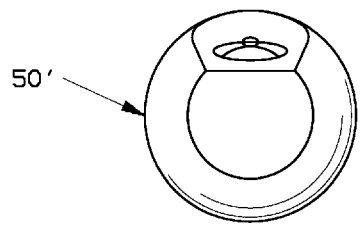
FIG. 5 is a right side view of the FIG. 4 abutment member.
Figure 6:
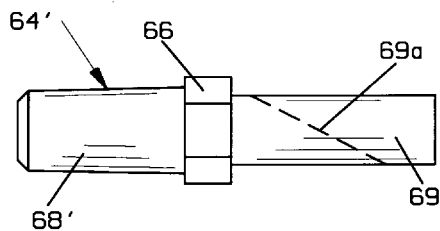
FIG. 6 is a plan view of an anti-rotation post member used with the FIGS. 4–5 abutment member.
Figure 7:
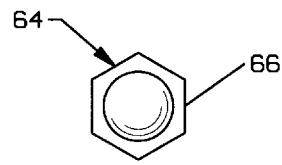
FIG. 7 is a right side view of the FIG. 6 anti-rotation post member.

In the event that the dentist has not drilled the root member receiving cavity deeply enough and shoulder 30 is disposed above crest 22 or gingiva 18 then a portion of the root member shoulder and a portion of the abutment post which is received in the root member will be visible thereby detracting from the aesthetic appearance of the patient. In accordance with the invention this can be remedied by use of a two part abutment as shown in Figs. 2–8. With particular reference to FIGS. 2 and 3, an abutment member 50 comprises a basal end portion 52 having an outer generally hemispherical surface portion similar to basal portion 44 of FIG. 1 and a generally frusto-conical portion which serves as a crown mounting portion 54 extending therefrom. Portion 54 is preferably provided with one or more anti-rotational flat surface portions as desired, not shown, to prevent rotational movement of a crown mounted thereon. The crown receiving frusto-conical portion 54 has a longitudinal axis 60 which can extend at a selected angle with the longitudinal axis 62 of bore 56 in order to provide the dentist with a choice of angles he can use to accomplish proper alignment of the crown with the natural teeth or other implants within the alveolar bone. For example, a series of abutments can be provided having different angles between the axes including 0, 15 25, 30 degrees.

A bore 56 having a non-circular surface 57 with respect to a horizontal cross section extends through mounting portion 54 down through basal end portion 52. A root member shoulder receiving seat 58 having a circular horizontal cross sectional configuration is formed in the basal end portion of bore 56 preferably having a taper slightly different from the taper of shoulder 26 of root member 10. That is, the taper of seat 58 is preferably less than the taper of shoulder 26 so that the lower portion of seat 58 as seen in the drawing is assured of forming a seal with shoulder 26 preventing cement, while in the liquid state, from seeping through into the soft tissue of a patient. The two part abutment includes an anti-rotation abutment mounting post 64. Post 64 has a head member 66 having a non-circular horizontal cross sectional shape matching that of surface 57 at one end and a locking taper on the shank portion 68 extending therefrom matching the female taper of socket 28. Shank portion 68 is received in socket 28 and abutment 50 is placed on shoulder 26 with the non-circular head member received in the non-circular matching portion 57 of bore 56 to prevent rotation of the abutment relative to the abutment post. Preferably bore 56 is formed sufficiently larger than the circumference of head member 66 so that excess liquid cement will be allowed to escape through the annular opening between head member 66 and bore 56 at the top of the abutment member to be further descussed below.

In practice, head member 66 can be provided having a standard length suitable for use with abutment members having bores formed at any of the selected angles referenced above and the excess, if any, can be removed after placement of the abutment on the root member in a chair side procedure.

Figure 8:
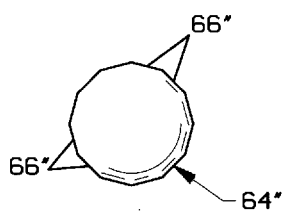
FIG. 8 is a side view of a modified anti-rotation post member.

As shown in FIGS. 2 and 3, the non-circular cross sectional surface is hexagonal however any selected number of faces can be employed as desired. For example, the bore could be formed with twelve face surfaces for reception of a post 64" having twelve face surfaces 66" as shown in FIG. 8. In general, the greater the number of faces the greater the ability to control the desired angular position of the abutment member Thus when the shoulder 26 of root member 10 projects above bone crest 22 or gingiva 18 the dentist can use a sulcus reamer to prepare the site around the shoulder to receive the generally hemispherical outer surface portion of basal end portion 52 which then can be fitted onto the shoulder. The appropriate abutment having the desired orientation of the crown mounting portion is selected and then the anti-rotation post is inserted through bore 56 and the abutment member is placed on shoulder 26. The anti-rotation post 64 is then tapped into locking engagement with socket 28. The non-circular configuration of head 66 and portion 57 of bore 56 prevent rotational movement of abutment member 50. The abutment member can be removed and suitable cement 70 placed in bore 56. The abutment member can then be replaced on mounting post 64 and shoulder 26 to lock the abutment member firmly to post 64 and root member 10. If desired, other locking means can be employed, such as a transversely extending pin or screw member 72 received through a transversely extending bore in head 66 into a transversely extending bore formed in the abutment member 50.

With reference to FIGS. 4–7, a modified embodiment is shown in which abutment member 50' has a circular bore 56' extending from crown mounting portion 54' to basal end portion 52' with non-circular head receiving seat 72 formed in communication with shoulder receiving seat 58'. Seat 72 forms a shoulder 74 with the circular portion of bore 56'. In this embodiment post 64' has a cylindrical portion 69 which extends from head portion 66 which is received in circular bore 56'. Depending upon which angular configuration is selected for abutment member 50' that part of the cylindrical portion 69 extending beyond bore 56' is removed as indicated by dashed line 69a. As in the FIG. 2, 3 embodiment, post 64' is inserted and tapped into socket 28 for locking engagement therewith, abutment 50' is placed onto shoulder 26 at the proper angular rotational angle and then prior to final seating cement is injected or placed onto the hexagonal surfaces of the internal aspect of the abutment to lock the abutment to the post member.

Figure 9:
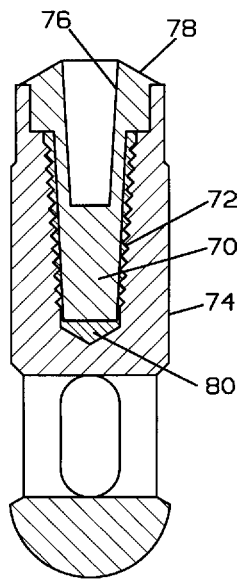
FIG. 9 is a cross sectional view of an adaptor mounted in a root member having an internal threaded bore for use with the two part abutment of the present invention.

FIG. 9 shows an adaptor 70 which can be used with root members having an internally threaded bore intended for reception of a threaded member which typically has a threaded bore leaving a thin wall threaded on opposed sides thereof, i.e., both inside and outside surfaces. Such members are prone to breakage due to their small size and the forces to which they are subjected in use. Adaptor 70 is a generally cylindrical member having an unthreaded outer surface received in threaded bore 72 of root member 74 for cementing therein. Adaptor 70 is formed with an internal bore 76 having a locking taper adapted to receive shank 68 or 68' of post 64, 64' respectively, having a matching locking taper described above. Adaptor 70 is formed with a shoulder 78 adapted to receive abutment member 50 or 50' in the same manner as described above in relation to FIGS. 2–8. Adaptor 70 is similar to root member 10 disclosed in U.S. Pat. No. 4,738,623, referenced supra, but without anchoring fins 20. As stated above, adaptor 70 is permanently placed in bore 72 by means of conventional cement 80. By using adaptor 70 a conventional root member having a threaded bore can be converted to use the stronger two part abutment system of the invention including a post having a locking taper with its concomitant advantages including providing an infinite number of angular positions, as well as substantially obviating breakage problems.

Figure 10:
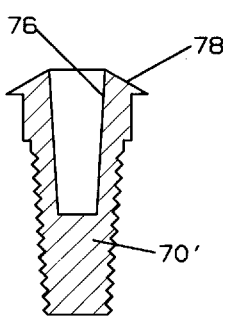
FIG. 10 is a cross sectional view of an adaptor similar to that of FIG. 9 but provided with a threaded outer surface.

FIG. 10 shows a modified adaptor 70' which is provided with a threaded outer surface for threading engagement in threaded bore 72 of root member 74. Preferably a longitudinally extending channel (not shown) is formed through the threads to permit passage of cement 80 therethrough. Adaptor 70' in other respects is the same as adaptor 70 so that its further desription need not be repeated.

Figure 11:
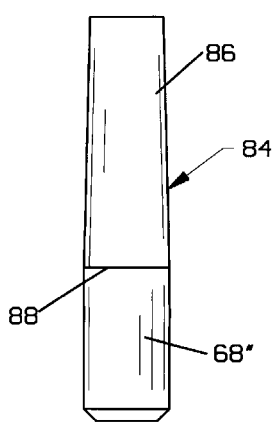
FIG. 11 is a plan view of an anti-rotation post member in another embodiment of the invention.

FIG. 11 shows a modified post 84 having a first locking taper section 68" at one end thereof for reception in socket 28 identical to post sections 68, 68' discussed above and a second locking taper section 86 at the opposite end thereof with the diameter of each section decreasing in a direction going from a generally central transition location 88 out to respective distal ends. Section 86 is adapted for receipt in a bore of an abutment having a matching locking taper, i.e., bore 56' in FIG. 4 modified to have a locking taper. Thus, section 86 prevents rotation as well as serving to lock the abutment to the root member.

Although the invention has been described with regard to specific preferred embodiments thereof, variations and modifications will become apparent to those skilled in the art. It is therefore the intention that the appended claims be interpreted as broadly as possible in view of the prior art to include all such variations and modifications.

What is claimed:

1. A dental implant system comrising a generally elongated root member having first and second ends, an opening formed in the first end and a shoulder formed at the first end circumscribing the opening, an abutment member having a basal end with a smooth curved outer surface area and a crown mounting portion extending therefrom, a bore extending from the crown mounting portion through the basal end, a root member shoulder receiving seat formed at the basal end of the bore, the seat having a surface generally conforming to the shoulder of the root member, a non-circular surface formed in at least a portion of the bore adjacent the shoulder receiving seat, an abutment mounting post having a shank extending from a head portion, the head portion having a non-circular configuration matching that of the non-circular surface of the bore, the shank lockably received in the opening in the root member in any selected angular orientation and the root member shoulder receiving seat of the abutment member received on the shoulder of the root member with the head portion received in the bore at the non-circular surface, and locking means to lock the abutment member to the abutment mounting post whereby the abutment member can be placed on the shoulder of the root member with the head portion of the abutment mounting post received in the bore at the non-circular surface and the abutment member and post adjusted to any selected angular orientation and then being locked in the opening in the root member with the abutment member and head portion in the selected angular orientation.

2. A dental implant system according to claim 1 in which the crown mounting portion of the abutment is generally frusto-conical in shape.

3. A dental implant system according to claim 1 in which the smooth curved outer surface area of the abutment is generally a partial hemispherical surface.

4. A dental implant system according to claim 1 in which the locking means comprises cement.

5. A dental implant system according to claim 1 in which the locking means comprises a pin extending transversely in the abutment across the bore.

6. A dental implant system according to claim 5 in which the pin is threaded.

7. A dental implant system according to claim 1 in which the crown mounting portion is generally frusto-conical having a first longitudinal axis and the bore has a second longitudinal axis which intersects the first longitudinal axis.

8. A dental implant system according to claim 1 in which the non-circular surface is hexagonal.

9. A dental implant system according to claim 1 in which the non-circular surface is twelve sided.

10. A dental implant system according to claim 1 in which the shank of the abutment mounting post is formed with a locking taper.

11. A dental implant system comprising a generally elongated root member having first and second ends, an opening formed in the first end and a shoulder formed at the first end circumscribing the opening, an abutment member having a basal end with a smooth curved outer surface area and a crown mounting portion extending therefrom, a bore extending from the crown mounting portion through the basal end, a root member shoulder receiving seat formed at the basal end of the bore, the seat having a surface generally conforming to the shoulder of the root member, a non-circular surface formed in at least a portion of the bore adjacent the shoulder receiving seat, an abutment mounting post having a shank extending from a head portion, the head portion having a non-circular configuration matching that of the non-circular surface of the bore, the shank lockably received in the opening in the root member and the root member shoulder receiving seat of the abutment member received on the shoulder of the root member with the head portion received in the bore at the non-circular surface, the shoulder of the root member and the root member shoulder receiving seat being frusto-conical having different tapers with the taper of the root member shoulder receiving seat being less than the taper of the root member so that a seal is formed at the lower portion of the abutment, member to prevent liquid cement from passing therethrough, and locking means to lock the abutment member to the abutment mounting post.

12. A dental implant system according to claim 11 in which the shank of the abutment mounting post is formed with a locking taper.

13. A dental implant system in which a generally elongated root member having first and second ends has a threaded bore extending into the root member through the first end, comprising an elongated generally tubular adaptor having an outer surface for reception in the threaded bore, the adaptor having a first end and having an opening formed in the first end and a shoulder circumscribing the opening, an abutment member having a basal end with a smooth curved outer surface area and a crown mounting portion extending therefrom, a bore extending from the crown mounting portion through the basal end, an adaptor shoulder receiving seat formed at the basal end of the bore, the seat having a surface conforming to the shoulder of the adaptor, a non-circular surface formed in at least a portion of the bore adjacent the shoulder receiving seat, an abutment mounting post having a shank extending from a head portion, the head portion having a non-circular configuration matching that of the non-circular surface of the bore, the shank lockably received in the opening in the adaptor and the adaptor shoulder receiving seat of the abutment member received on the shoulder of the adaptor with the head portion received in the bore at the non-circular surface, and locking means to lock the abutment member to the abutment mounting post.

14. A dental implant system according to claim 13 in which the outer surface of the adaptor is unthreaded and further comprising cement to lock the adaptor in the threaded bore of the root member.

15. A dental implant system according to claim 13 in which the outer surface of the adaptor is threaded for reception in the threaded bore of the root member.

* * * * *